US009642737B2

(12) United States Patent
Seres et al.

(10) Patent No.: US 9,642,737 B2
(45) Date of Patent: May 9, 2017

(54) PORTABLE LEVEL SENSOR (71) Applicant: Seres Healthcare Limited, Greater London (GB)

(72) Inventors: Michael Seres, Hertfordshire (GB); Adam Bloom, London (GB); James Hutchinson, Cambridgeshire (GB); Nigel Tozer, Oxfordshire (GB); Steven Barlow, Cambridgeshire (GB)

(73) Assignee: SERES HEALTHCARE LIMITED, London, Greater London (GB)

( * ) Notice: Subject to any disclaimer, the term of this patent is extended or adjusted under 35 U.S.C. 154(b) by 0 days.

(21) Appl. No.: 14/654,900

(22) PCT Filed: Dec. 20, 2013

(86) PCT No.: PCT/GB2013/053380
§ 371 (c)(1),
(2) Date: Jun. 23, 2015

(87) PCT Pub. No.: WO2014/102537
PCT Pub. Date: Jul. 3, 2014

(65) Prior Publication Data
US 2015/0342777 A1  Dec. 3, 2015

(30) Foreign Application Priority Data

Dec. 24, 2012  (GB) .................................. 1223353.2

(51) Int. Cl.
*A61B 5/20* (2006.01)
*A61F 5/44* (2006.01)
(Continued)

(52) U.S. Cl.
CPC ............ *A61F 5/4404* (2013.01); *A61B 5/208* (2013.01); *A61B 10/0045* (2013.01);
(Continued)

(58) Field of Classification Search
CPC . A61B 10/007; A61B 2090/063; A61B 5/208; A61B 5/20; A61B 10/0045;
(Continued)

(56) References Cited

U.S. PATENT DOCUMENTS 4,291,692 A  *  9/1981  Bowman ............ A61B 5/14507
                                                   604/151
5,135,485 A  *  8/1992  Cohen ................ A61M 5/1684
                                                   324/606
(Continued)

FOREIGN PATENT DOCUMENTS

EP      2227033 A2     9/2010
JP      H09-29001      2/1997
(Continued)

OTHER PUBLICATIONS

Written opinion of the International Preliminary Examining Authority dated Sep. 3, 2014 for Application No. PCT/GB2013/053380.
(Continued)

*Primary Examiner* — Van Trieu
(74) *Attorney, Agent, or Firm* — The Dobrusin Law Firm, P.C.

(57) ABSTRACT

A portable level sensor for a flexible bag for collecting a fluid and/or a solid, and a system and method for sensing the content level of a flexible bag using the portable level sensor. The sensor comprises a flexible resistor element with an electrical resistance that changes in dependence upon its degree of flexing, means for attaching the resistor element to an outside surface of the flexible bag and means for periodically polling the electrical resistance of the resistor element and transmitting to a receiver a signal which varies in dependence on the said electrical resistance.

19 Claims, 3 Drawing Sheets

(51) Int. Cl.
  *A61F 5/445* (2006.01)
  *A61B 10/00* (2006.01)
  *A61B 90/00* (2016.01)
(52) U.S. Cl.
  CPC ............ *A61B 90/06* (2016.02); *A61F 5/44* (2013.01); *A61F 5/445* (2013.01); *A61B 2090/063* (2016.02)
(58) Field of Classification Search
  CPC ............ A61B 10/0048; A61B 10/0051; A61B 2090/06; A61B 2090/061; A61M 2205/14; A61M 2205/3379; G01F 1/007; G01F 1/05
  See application file for complete search history.

(56) References Cited

U.S. PATENT DOCUMENTS

| | | | |
|---|---|---|---|
| 5,157,372 A | 10/1992 | Langford | |
| 5,260,692 A | 11/1993 | Claren | |
| 5,439,001 A * | 8/1995 | Butterfield | A61B 5/02233 600/485 |
| 6,219,933 B1 * | 4/2001 | Taniguchi | B41F 31/02 347/7 |
| 6,696,964 B1 | 2/2004 | Hakansson | |
| 7,002,054 B2 | 2/2006 | Allen et al. | |
| 8,544,341 B2 * | 10/2013 | Grumbles | E03D 13/005 4/661 |
| 8,850,897 B2 * | 10/2014 | Eichhorn | B82Y 15/00 73/774 |
| 2004/0230181 A1 * | 11/2004 | Cawood | A61F 5/453 604/544 |
| 2009/0281497 A1 * | 11/2009 | Kamen | A61M 5/1413 604/151 |
| 2009/0314101 A1 * | 12/2009 | Levine | A61F 5/44 73/861.08 |
| 2011/0264033 A1 * | 10/2011 | Jensen | A61M 5/1452 604/65 |
| 2013/0012896 A1 | 1/2013 | Suzuki et al. | |
| 2013/0324952 A1 * | 12/2013 | Krystek | A61F 5/445 604/318 |
| 2015/0177079 A1 * | 6/2015 | Eichhorn | G01L 9/0054 73/774 |
| 2016/0101227 A1 * | 4/2016 | Norris | A61M 1/28 604/29 |

FOREIGN PATENT DOCUMENTS

| | | |
|---|---|---|
| JP | 2003-507720 | 2/2003 |
| JP | 2004-532713 | 10/2004 |
| JP | 2011-078791 | 4/2011 |
| JP | 2011-147505 | 8/2011 |
| WO | 94/15190 A | 7/1994 |
| WO | 01/13830 A1 | 3/2001 |
| WO | 2011/054045 | 5/2011 |

OTHER PUBLICATIONS

International Search Report dated Mar. 7, 2014 for Application No. PCT/GB2013/053380.
IPRP, Application No. PCT/GB2013/053380, dated Oct. 29, 2014.
Japanese Office Action dated Jul. 8, 2016 for Application No. 2015-548763.

* cited by examiner

PORTABLE LEVEL SENSOR

This invention relates to a portable level sensor for a flexible bag for collecting a fluid and/or a solid, and in particular, to a portable level sensor for a stoma bag or a bag for collecting urine.

The invention also relates to a system for sensing the content level of a flexible bag comprising the portable level sensor, and a method for sensing the content level of a flexible bag.

A stoma is an artificial opening in the abdomen, which connects a portion of the body cavity to the outside environment. A removable bag is adhered to the outside of the abdomen wall to collect waste leaving the body through the stoma. There are three main types of stoma: a ileostomy, an opening from the small intestine, to allow faeces to leave the body without passing through the large intestine; a colostomy, an opening from the large intestine, to allow faeces to leave the body without passing through the anus; and a urostomy, an opening from the ureters, to allow urine to leave the body without passing through the bladder. The term "stoma bag", as used herein is intended to cover any flexible bag that is used to collect body waste diverted from the ileum, colon or urinary tract.

A problem experienced by many stoma (or ostomy) bag users is that they have no means of knowing the extent to which the bag has been filled, and consequently when it needs to be emptied or changed. If the user does not monitor the bag and empty it in due time then the bag may overfill, burst, or detach itself from the user.

Monitoring devices are known for sensing the filling of a flexible bag.

U.S. Pat. No. 5,260,692, for example, describes the use of a sensor comprising an electrical resistance element having an electrical resistance that changes in dependence upon its degree of elastic stretching. The resistance element is stretched manually and is then mounted to an outside surface a stoma bag. When it is released, the resistance element contracts, forming a fold in the wall of the stoma bag. As the bag fills the fold is smoothed out under elastic stretching of the resistor element. At a predetermined resistance value an alarm is generated to alert the user that the bag is nearly full.

U.S. Pat. No. 6,696,964 describes the use of a sensor comprising an electric resistor element having an electric resistance that changes in dependence upon its degree of bending. The resistor element is inserted into a pocket attached to a flexible bag, such that as the bag fills, the bulging of the walls causes the resistor element to bend in the middle. At a predetermined resistance value an alarm is activated to inform the user that it is time to exchange the bag.

A problem with the sensing devices described in U.S. Pat. No. 5,260,692 and U.S. Pat. No. 6,696,964 however, is that a single alarm level is provided, so that between the bag being exchanged (i.e., the bag being empty) and the alarm sounding (i.e., the bag being nearly full), the stoma bag user has no knowledge of how full the bag is. A similar problem arises in catheterised patients with bags for collecting urine.

There is a need therefore to provide an improved device for sensing the filling of a flexible bag, in particular a stoma bag and a urine bag.

In a first aspect, the invention provides a portable level sensor for a flexible bag for collecting a fluid and/or a solid, wherein the sensor comprises a flexible resistor element, having an electrical resistance that changes in dependence upon its degree of flexing; means for attaching the resistor element to an outside surface of the flexible bag; and means for periodically polling the electrical resistance of the resistor element and transmitting to a receiver a signal which varies in dependence on the said electrical resistance.

Advantageously, by providing a portable level sensor with the ability to periodically poll the electrical resistance of the resistor element and transmit to a receiver a signal which varies in dependence on the said electrical resistance, a simple device in accordance with the invention is able to detect the progressive filling of a flexible bag and periodically report on its fullness level.

The flexible bag is preferably a stoma bag or a urine collection bag.

The flexible resistor element may be a commercially available resistor such as the so called "Flex Sensor" from Spectra Symbol, which has a flat resistance of 10K Ohms and a bend resistance range of from 60K to 110K Ohms. It will be appreciated that it is important that the relationship between electrical resistance and degree of flexing should remain consistent over multiple lifecycles of the flexible resistor element.

The flexible resistor element may extend substantially across the entire width of the flexible bag and may be fastened to the outside surface of the flexible bag with one or more clips. Preferably, a clip is provided at each end of the flexible resistor element to clamp the flexible resistor element to the surface of the flexible bag.

In order to prevent movement of the resistor element with respect to the outside surface of the flexible bag, the clip may include a plurality of inwardly directed teeth, adapted to engage with the outside surface of the bag and/or the resistor element.

In order to periodically poll the electrical resistance of the resistor element and transmit to a receiver a signal which varies in dependence on the said electrical resistance, the portable level sensor preferably comprises a communication module for transmitting a wireless signal to a receiver; and a microprocessor programmed and arranged to generate a digital signal corresponding to the electrical resistance of the resistor element and to communicate said digital signal to the communication module for wireless transmission to the receiver.

The communication module is preferably a Bluetooth sensor module. The Bluetooth sensor module may comprise a standard Bluetooth module and/or a Bluetooth low energy (BLE) module. The term "standard Bluetooth module" is used herein to refer to a Bluetooth module such as, but not limited to, a Bluetooth version 2.0+EDR (Enhanced Data Rates) module, while the term "Bluetooth low energy module" is used to refer to a Bluetooth module such as, but not limited to, a Bluetooth version 4.0 (Bluetooth smart).

The microprocessor is preferably a Peripheral Interface Controller (PIC), arranged to read the value of the flexible resistor element through an Analogue to Digital Converter (ADC).

The microprocessor and communication module may be incorporated into a small device able to be carried on the flexible bag and powered by a small battery, such as a 3V lithium coin cell. Preferably, the small device is housed within a clip.

In order to preserve battery life of the portable level sensor, the communication module may be switchable between an active mode and an idle mode, wherein the power consumption of the communication module in the idle mode is lower than in the active mode, and the microprocessor is preferably programmed to switch the communication module between the idle mode and the active mode by communicating the digital signal to the communication module. Preferably, the microprocessor is further programmed to switch the communication module from the active mode back into the idle mode.

The microprocessor may be programmed and arranged to generate a second digital signal corresponding to the voltage of the battery and to communicate said second digital signal to the communication module for wireless transmission to the receiver.

In order to determine the orientation of the flexible bag and transmit to the receiver a signal which varies in dependence on the orientation, the portable level sensor preferably comprises an accelerometer. The accelerometer may be programmed and arranged to generate a digital signal corresponding to the orientation of the flexible bag and to communicate said digital signal to the communication module for wireless transmission to the receiver. The accelerometer may be contained within the communication module.

In a second aspect, the invention provides a system for sensing the content level of a flexible bag comprising a portable level sensor as previously described and a wireless receiver adapted to receive the signal transmitted by the communication module and communicate the content level of the flexible bag to a user.

The wireless receiver is preferably a personal electronic device, for example, a laptop computer, a mobile phone or a tablet computer.

Preferably, the receiver includes means for advising the user of the subsistence of a wireless link between the receiver and the communication module. Preferably, the receiver also includes a visual display for presenting to the user a visual representation of the content level of the bag. This may, for example, be in the form of a percentage value or the filling of a scale bar.

The receiver may be programmed and arranged to communicate to the user the total volume of fluid and/or solid collected by the flexible bag over a time period selected by the user. In addition, the receiver may be programmed to communicate the total volume of fluid and/or solid collected by the flexible bag over the specified time period to a third party, such as the users physician.

When the portable level sensor comprises an accelerometer, the receiver may be programmed and arranged to communicate to the user a corrected value for the total volume of fluid and/or solid collected by the flexible bag which has been adjusted to account for the orientation of the flexible bag. This may, for example, be done by calibrating the accelerometer with respect to the upright position, so as to detect the degree of deviation from the upright position, and correlating the value of electrical resistance of the resistor element to the actual content level of the flexible bag when the bag is orientated at one or more degrees of deviation from the upright position.

In order to alert the user when the content level of the bag exceeds a predetermined threshold, the receiver preferably includes an alarm. Advantageously, more than one threshold level may be selected by the user to activate the alarm.

The alarm may be a vibrational, visible and/or audible alarm, and may be selected by the user.

In order to alert the user to a possible mechanical failure of the attachment of the resistor element to the flexible bag or to a potential leakage in the bag, an alarm is preferably activated when the signal received from the communication module indicates a decrease in the content level of the flexible bag.

Preferably, the receiver further includes means for determining whether the signal indicating a decrease in the content level of the flexible bag is associated with a mechanical failure of the attachment of the resistor element to the flexible bag or with movement of the bag.

When the flexible bag is a stoma bag, the receiver may also include means for detecting patterns of signals associated with the stoma bag user adopting a sitting or prone position.

In a third aspect, the invention provides a method for sensing the content level of a flexible bag comprising using the portable level sensor as described above.

A preferred embodiment of the invention will be further described with reference to the accompanying drawings in which.

Figure 1:
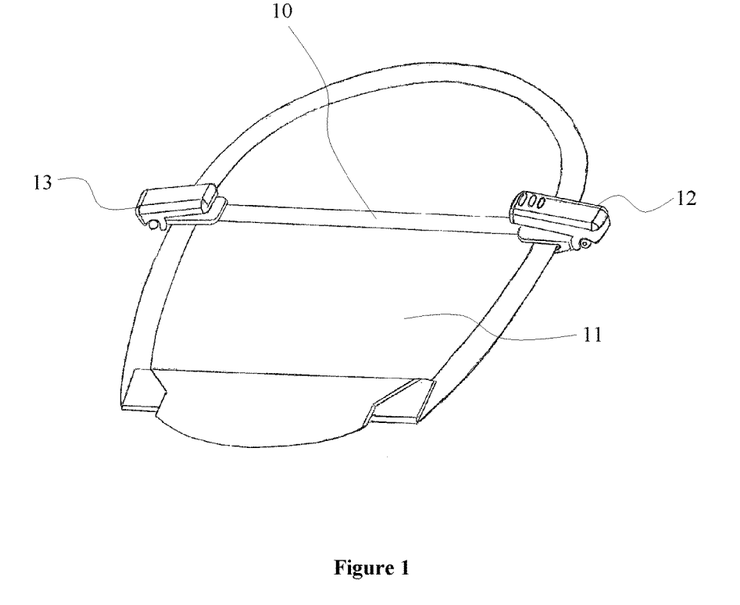
FIG. 1 is a perspective view of a flexible bag having a portable level sensor in accordance with the invention mounted thereon.
Figure 2:
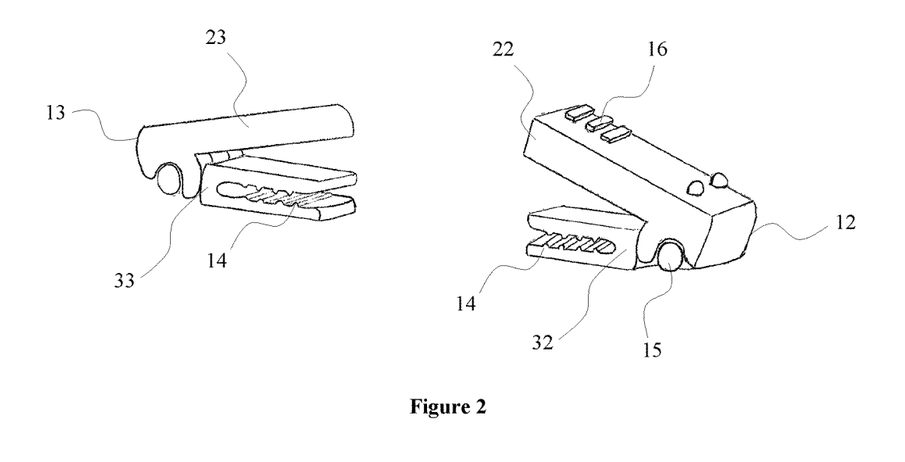
FIG. 2 is an enlarged view of the means for attaching the resistor element to an outside surface of the flexible bag.
Figure 3:
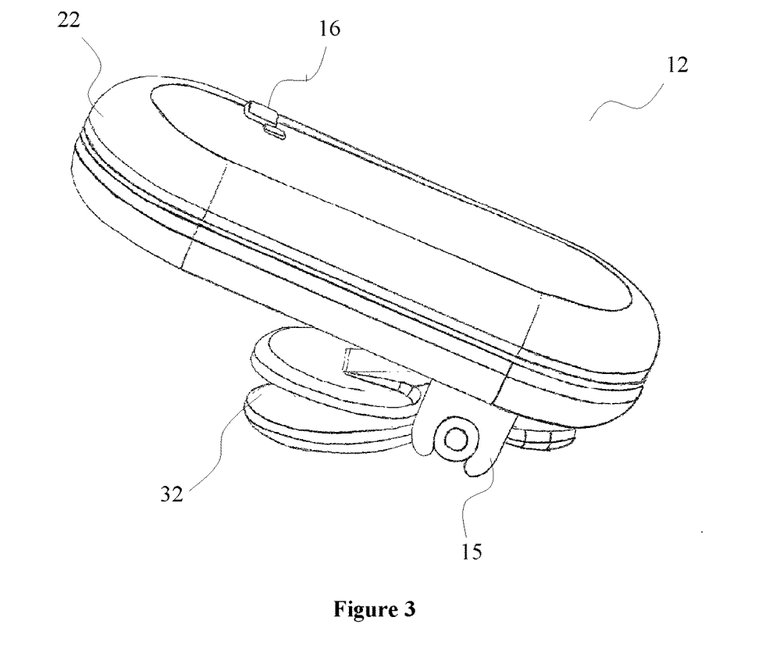
FIG. 3 is a perspective view of an alternative means for attaching the resistor element to an outside surface of the flexible bag.

The embodiment shown in FIGS. 1-3 includes a flexible resistor element 10 which extends substantially across the entire width of the flexible bag 11 and is attached to the flexible bag 11 by clips 12 and 13.

The resistor element 10 includes an active portion having an electrical resistance that changes in dependence upon its degree of flexing; a resilient casing to facilitate "spring back" of the element after it has been flexed; and two conductor wires. The conductor wires are connected to the active portion such that the active portion is connected in series between them. The wires are arranged such that the free end of each wire extends out of the same end of the resilient casing and terminates within clip 12.

The clips 12, 13 have a top portion 22, 23 and a clamp portion 32, 33. The top portion 22, 23 is connected to the clamp portion 32, 33 by a hinge device 15, which allows the top portion 22, 23 to rise as the flexible bag fills. A plurality of inwardly directed teeth 14 are formed on the inside surface of the clips 12, 13 to grip the outside surface of the bag 11 and/or the resistor element 10.

Figure 4:
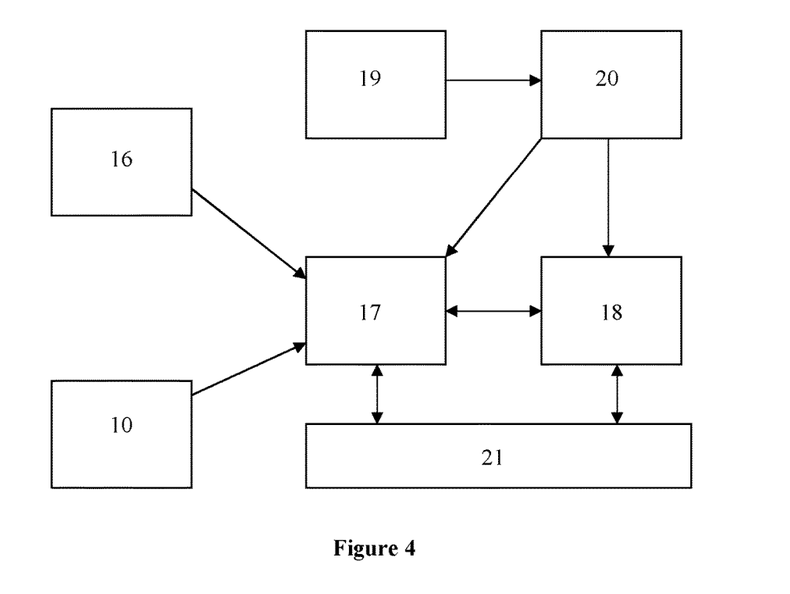
FIG. 4 is a schematic diagram showing how the component parts of the portable level sensor interact with one another.

A schematic diagram of the electronic function is shown in FIG. 4. The flexible resistor element 10 is connected to the microprocessor 17, which periodically polls the electrical resistance of the resistor element 10 and converts it to a digital signal by means of an on-board Analogue to Digital Converter (ADC). The digital signal corresponding to the electrical resistance is output periodically (for example, every 1, 2 or 5 minutes), to a Bluetooth module 18, which is programmed to transmit the signal to a receiver via Bluetooth.

As shown in FIG. 4 the microprocessor 17 and Bluetooth module 18 are powered by a small battery 19 via a switching regulator 20. Both the microprocessor 17 and the Bluetooth module 18 are connected to a debug connector 21 to facilitate programming by conventional methods. The microprocessor 17 can be switched on or off by button 16.

The microprocessor 17, Bluetooth module 18, battery 19, switching regulator 20 and the debug connector 21 are all housed within clip 12.

In use, the flexible resistor element 10 is fastened to the flexible bag 11 by clips 12 and 13, and the flexible bag 11 is attached to a stoma in the normal way. The two conductor wires of the resistor element 10 are connected (by a connector not shown) to the microprocessor 17, which reads the value of the flexible resistor element 10 through the Analogue to Digital Converter (ADC). The microprocessor 17 subsequently generates a digital signal corresponding to the electrical resistance of the resistor element 10 and communicates this signal to the Bluetooth module 18.

In use, the Bluetooth module 18 is paired to a receiver, such as a mobile phone, which runs an application, such as an android application.

Figure 5:
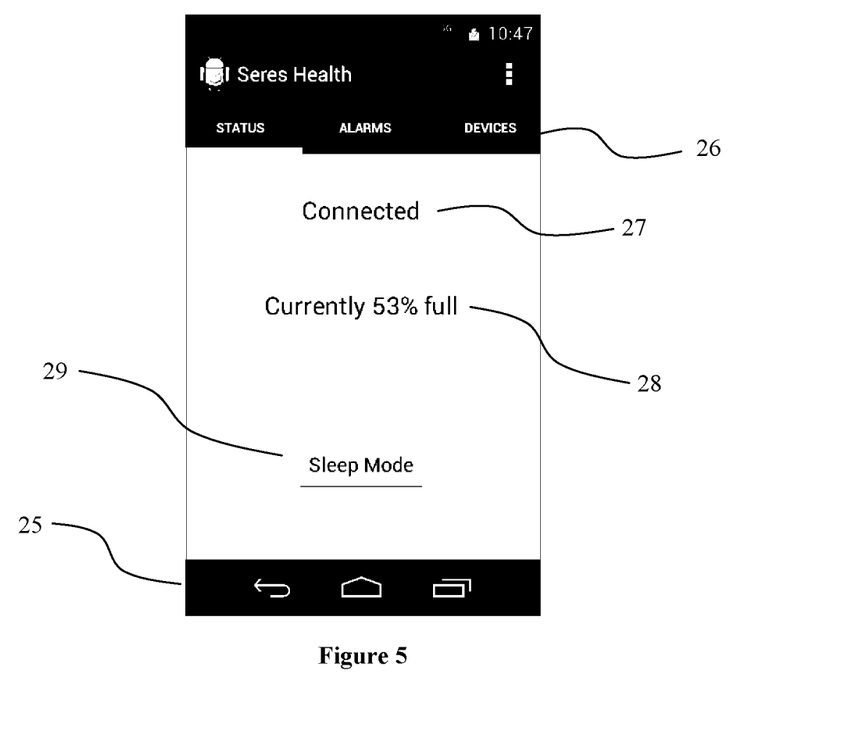
FIG. 5 is a screenshot of a typical Android application displaying the content level of the flexible bag.

A screen shot of a typical Android application is shown in FIG. 5. The screen shows the standard Android "home" and "back" buttons 25, and three tabs 26, labelled "Status", "alarms" and "devices", which provide navigation throughout the application.

The "status" display (shown in FIG. 5) is set up to advise the user of the current connection status 27 of the mobile phone and to provide the user with a visual representation of the current content level of the bag 28 (which in this embodiment is shown as a percentage of fullness). The "status" display also allows the user to switch the application into "sleep mode" 29, when the user is about to adopt a sitting or prone position.

In the "sleep mode" the application uses a set of stored reference data (correlating the value of electrical resistance of the resistor element 10 to the actual content level of the bag 11 when the user is lying down) to interpret the signal received from the Bluetooth module and adjust the "apparent" content level of the bag 11 accordingly. This allows the portable level sensor of the present invention to accurately detect the progressive filling of the flexible bag 11 even when the user adopts a sitting or prone position (as compared to standing).

The application includes a user interface which allows the user to set one or more alarms in order to alert the user when the content level of the bag exceeds a predetermined threshold level. The user interface also allows the user to edit the settings of the alarm, including, for example, its melody, volume, or duration, and also allows for an alarm to be removed or cancelled.

As well as showing the user the current Bluetooth module which is pair to the mobile phone (if any), the application also allows the user to scan for other modules, and pair them with the mobile phone. The application also allows the user to un-pair the mobile phone from a paired Bluetooth module.

The application is able to produce an output graph, plotting the volume of fluid and/or solid collected by the bag over a time period selected by the user. In addition, the application can store the user's details, such as name, patient number and their physician's email address and can be programmed to send these output graphs to the user's physician.

In a preferred embodiment, the communication module comprises an accelerometer and the user interface of the application is configured to allow the user to calibrate the accelerometer with respect to an upright position of the bag, and thereby to generate a value corresponding to a degree of deviation from the upright position. The accelerometer can be calibrated in a number of orientations, including, for example, when the user is standing upright, lying down and lying sideways.

On receiving a digital signal corresponding to the orientation of the bag 11 the application uses a set of stored reference data (correlating the value of electrical resistance of the resistor element 10 to the actual content level of the bag 11 when the bag 11 is so orientated) to interpret the signal and adjust the "apparent" content level of the bag 11 accordingly. For example, if the accelerometer signals that the bag 11 is orientated such that it is 20% upright and 80% lying down (i.e., the user is reclined), the application will calculate the actual content level of bag 11 by correlating the value of electrical resistance of the resistor element 10 to the actual content level of the bag 11 when the user is (i) standing upright and (ii) lying down, and adding together 20% of value (i) and 80% of value (ii). This allows the portable level sensor of the present invention to accurately detect the progressive filling of the flexible bag 11 even when the bag is orientated at one or more degrees of deviation from the upright position.

The invention claimed is:

1. A portable level sensor for a flexible bag that is a stoma bag or a urine collection bag for collecting a fluid and/or a solid, wherein the portable level sensor comprises:
   a flexible resistor element, having an electrical resistance that changes in dependence upon its degree of flexing;
   means for attaching the flexible resistor element to an outside surface of the flexible bag; and
   means for periodically polling the electrical resistance of the flexible resistor element and transmitting to a receiver a signal which varies in dependence on the said electrical resistance; and
   comprising an accelerometer programmed and arranged to generate a digital signal corresponding to an orientation of the flexible bag and transmit to a receiver a signal which varies in dependence on the orientation of the flexible bag.

2. The portable level sensor as claimed in claim 1, wherein said means for periodically polling the electrical resistance of the flexible resistor element and transmitting to a receiver a signal which varies in dependence on the said electrical resistance comprises:
   (a) a communication module for transmitting a wireless signal to a receiver; and
   (b) a microprocessor programmed and arranged to generate a digital signal corresponding to the electrical resistance of the flexible resistor element and to communicate said digital signal to the communication module for wireless transmission to the receiver.

3. The portable level sensor as claimed in claim 1, wherein said means for periodically polling the electrical resistance of the flexible resistor element and transmitting to a receiver a signal which varies in dependence on the said electrical resistance comprises:
   (a) a communication module for transmitting a wireless signal to a receiver; and
   (b) a microprocessor programmed and arranged to generate a digital signal corresponding to the electrical resistance of the flexible resistor element and to communicate said digital signal to the communication module for wireless transmission to the receiver;
   and wherein the communication module is switchable between an active mode and an idle mode, wherein power consumption of the communication module in the idle mode is lower than in the active mode, and wherein the microprocessor is programmed to switch the communication module between the idle mode and the active mode by communicating the digital signal to the communication module.

4. A system for sensing a content level of the flexible bag that is a stoma bag or a urine collection bag comprising:
   the portable level sensor according to claim 1, wherein said means for periodically polling the electrical resistance of the flexible resistor element and transmitting to a receiver a signal which varies in dependence on the said electrical resistance comprises:
(a) a communication module for transmitting a wireless signal to a receiver; and
(b) a microprocessor programmed and arranged to generate a digital signal corresponding to the electrical resistance of the flexible resistor element and to communicate said digital signal to the communication module for wireless transmission to the receiver; and
a wireless receiver adapted to receive the wireless signal transmitted by the communication module and communicate the content level of the flexible bag to a user.

5. A system for sensing a content level of the flexible bag that is a stoma bag or a urine collection bag comprising:
the portable level sensor according to claim 1, wherein said means for periodically polling the electrical resistance of the flexible resistor element and transmitting to a receiver a signal which varies in dependence on the said electrical resistance comprises:
(a) a communication module for transmitting a wireless signal to a receiver; and
(b) a microprocessor programmed and arranged to generate a digital signal corresponding to the electrical resistance of the flexible resistor element and to communicate said digital signal to the communication module for wireless transmission to the receiver; and
a wireless receiver adapted to receive the wireless signal transmitted by the communication module and communicate the content level of the flexible bag to a user, wherein the wireless receiver includes an alarm for alerting the user when the content level of the flexible bag exceeds a predetermined threshold.

6. A system for sensing a content level of the flexible bag that is a stoma bag or a urine collection bag comprising:
the portable level sensor according to claim 1, wherein said means for periodically polling the electrical resistance of the flexible resistor element and transmitting to a receiver a signal which varies in dependence on the said electrical resistance comprises:
(a) a communication module for transmitting a wireless signal to a receiver; and
(b) a microprocessor programmed and arranged to generate a digital signal corresponding to the electrical resistance of the flexible resistor element and to communicate said digital signal to the communication module for wireless transmission to the receiver; and
a wireless receiver adapted to receive the wireless signal transmitted by the communication module and communicate the content level of the flexible bag to a user, wherein said wireless receiver includes means for alerting the user when the wireless signal received from the communication module indicates a decrease in the content level of the flexible bag and means for determining whether the wireless signal indicating a decrease in the content level of the flexible bag is associated with a mechanical failure of the attachment of the flexible resistor element to the flexible bag or with movement of the flexible bag.

7. A system for sensing a content level of the flexible bag that is a stoma bag or a urine collection bag comprising:
the portable level sensor according to claim 1, wherein said means for periodically polling the electrical resistance of the flexible resistor element and transmitting to a receiver a signal which varies in dependence on the said electrical resistance comprises:
(a) a communication module for transmitting a wireless signal to a receiver; and
(b) a microprocessor programmed and arranged to generate a digital signal corresponding to the electrical resistance of the flexible resistor element and to communicate said digital signal to the communication module for wireless transmission to the receiver; and
a wireless receiver adapted to receive the wireless signal transmitted by the communication module and communicate the content level of the flexible bag to a user, wherein the flexible bag is a stoma bag and the wireless receiver includes means for detecting patterns of signals associated with a stoma bag user adopting a sitting or prone position.

8. A method for sensing a content level of a flexible bag comprising:
(a) providing a flexible resistor element having an electrical resistance that changes in dependence upon its degree of flexing attached to an outside surface of the flexible bag, such that the flexible resistor element flexes upon filling of the flexible bag; and
(b) periodically polling the electrical resistance of the flexible resistor element and transmitting to a receiver a signal which varies in dependence on the said electrical resistance;
wherein the flexible bag is a stoma bag or a urine collection bag.

9. The method as claimed in claim 8, in which the periodical polling of step (b) is carried out by a means comprising:
(a) a communication module for transmitting a wireless signal to a receiver; and
(b) a microprocessor programmed and arranged to generate a digital signal corresponding to the electrical resistance of the flexible resistor element and to communicate said digital signal to the communication module for wireless transmission to the receiver.

10. The method as claimed in claim 8, in which the periodical polling of step (b) is carried out by a means comprising:
(a) a communication module for transmitting a wireless signal to a receiver; and
(b) a microprocessor programmed and arranged to generate a digital signal corresponding to the electrical resistance of the flexible resistor element and to communicate said digital signal to the communication module for wireless transmission to the receiver; and
the method further comprising switching the communication module from an idle mode to an active mode by communicating the digital signal from the microprocessor to the communication module.

11. The method as claimed in claim 8, further comprising receiving the transmitted signal, wherein the signal is wireless, to a wireless receiver and communicating the content level of the flexible bag to a user.

12. The method as claimed in claim 8, further comprising alerting a user when the content level of the flexible bag exceeds a predetermined threshold.

13. The method as claimed in claim 9, further comprising alerting a user when the wireless signal received from the communication module indicates a decrease in the content level of the flexible bag and determining whether the wireless signal indicating a decrease in the content level of the flexible bag is associated with a mechanical failure of the attachment of the flexible resistor element to the flexible bag or with movement of the flexible bag.

14. The method as claimed in claim 8, wherein the flexible bag is a stoma bag and the method further comprises a step of detecting patterns of signals associated with a stoma bag user adopting a sitting or prone position.

15. A system for simultaneously sensing a content level of a plurality of flexible bags comprising:
   (a) a plurality of portable level sensors according to claim 1; and
   (b) a wireless receiver adapted to receive the signal transmitted by the communication module of each said portable level sensor and to communicate the content level of each flexible bag to a monitoring station.

16. A method for simultaneously sensing a content level of a plurality of flexible bags, said method comprising:
   (a) attaching a plurality of portable level sensors according to claim 1 to an outside surface of each of the plurality of flexible bags, such that the flexible resistor element flexes upon filling of the flexible bag;
   (b) periodically polling the electrical resistance of each flexible resistor element and transmitting to a receiver a separate signal corresponding to the electrical resistance of each flexible resistor element which varies in dependence on the said electrical resistance; and
   (c) receiving the transmitted signal, wherein the signal is wireless, to a wireless receiver and communicating the content level of the flexible bag to a monitoring station.

17. A portable level sensor for a flexible bag for collecting a fluid and/or a solid, wherein the portable level sensor comprises:
   a flexible resistor element, having an electrical resistance that changes in dependence upon its degree of flexing;
   means for attaching the flexible resistor element to an outside surface of the flexible bag;
   means for periodically polling the electrical resistance of the flexible resistor element and transmitting to a receiver a signal which varies in dependence on the said electrical resistance; and
   an accelerometer programmed and arranged to generate a digital signal corresponding to an orientation of the flexible bag and transmit to a receiver a signal which varies in dependence on the orientation of the flexible bag.

18. A system for sensing the content level of a flexible bag comprising the portable level sensor according to claim 17 and a receiver adapted to receive the digital signal transmitted by the accelerometer, wherein the receiver comprises means for calculating the actual content level of the flexible bag when the flexible bag is orientated at one or more degrees of deviation from an upright position and means for communicating the actual content level of the flexible bag to a user.

19. A method for sensing the content level of a flexible bag comprising
   (a) providing the portable level sensor according to claim 17 attached to an outside surface of the flexible bag, such that the flexible resistor element flexes upon filling of the flexible bag;
   (b) periodically polling the electrical resistance of the flexible resistor element and transmitting to a receiver a signal which varies in dependence on the said electrical resistance; and
   (c) transmitting to the receiver a signal from the accelerometer which varies in dependence on the orientation of the flexible bag.

* * * * *

UNITED STATES PATENT AND TRADEMARK OFFICE
CERTIFICATE OF CORRECTION

| | | |
|---|---|---|
| PATENT NO. | : 9,642,737 B2 | Page 1 of 1 |
| APPLICATION NO. | : 14/654900 | |
| DATED | : May 9, 2017 | |
| INVENTOR(S) | : Michael Seres et al. | |

It is certified that error appears in the above-identified patent and that said Letters Patent is hereby corrected as shown below:

In the Claims

Column 10 Line 20, Claim 19:
After "flexible bag comprising" insert --:--

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*